US008620419B2

(12) United States Patent
Rotenberg et al.

(10) Patent No.: US 8,620,419 B2
(45) Date of Patent: *Dec. 31, 2013

(54) MULTI PURPOSE CRITERIA BASED ADAPTIVE TRAINING SYSTEM

(75) Inventors: Edward Rotenberg, Groton, MA (US); Patrice D. Tremoulet, Moorestown, NJ (US); Randel A. Crowe, Interlachen, FL (US); Ruthann Savage-King, Groton, MA (US); Patrick Craven, Merchantville, NJ (US); Steven J. Tourville, Orlando, FL (US)

(73) Assignee: Lockheed Martin Corporation, Bethesda, MD (US)

( * ) Notice: Subject to any disclaimer, the term of this patent is extended or adjusted under 35 U.S.C. 154(b) by 494 days.

This patent is subject to a terminal disclaimer.

(21) Appl. No.: 12/558,164

(22) Filed: Sep. 11, 2009

(65) Prior Publication Data

US 2011/0066005 A1 Mar. 17, 2011

(51) Int. Cl.
*A61B 5/02* (2006.01)
(52) U.S. Cl.
USPC ........................................................ 600/544
(58) Field of Classification Search
USPC .............................................. 600/544–545
See application file for complete search history.

(56) References Cited

U.S. PATENT DOCUMENTS

| 5,724,987 | A | * | 3/1998 | Gevins et al. | 600/544 |
| 5,999,846 | A | * | 12/1999 | Pardey et al. | 600/544 |
| 8,271,077 | B1 | | 9/2012 | Rotenberg | |
| 2005/0221268 | A1 | | 10/2005 | Chaar | |

OTHER PUBLICATIONS

*Diagnostic and Statistical Manual of Mental Disorders, 3rd Edition, Revised*, Washington, DC American Psychiatric Association, (1987), 247-251.
Ballinger, J C, et al., "Consensus statement on posttraumatic stress disorder from the International Consensus Group on Depression and Anxiety", *J Clin Psychiatry*, 61(Suppl 5), (2000), 60-6.
Spira, James L, et al., "Chapter 10, Experiential Methods in the Treatment of Combat", *Combat stress injury : theory, research, and management*, New York : Routledge; Routledge Psychosocial Stress Series, (2007), 205-218.
Weathers, F., et al., "The PTSD Checklist (PCL): Reliability, Validity, and Diagnostic Utility", *Presented at the International Society of Traumatic Stress Studies*, San Antonio, TX, 1993, (1993), 3 pgs.
U.S. Appl. No. 12/548,056, Notice of Allowance mailed Jun. 8, 2012, 11 pgs.
U.S. Appl. No. 12/548,056, Notice of Allowance mailed Jul. 16, 2012, 5 pgs.

* cited by examiner

*Primary Examiner* — Particia Mallari
*Assistant Examiner* — Vasuda Ramachandran
(74) *Attorney, Agent, or Firm* — Schwegman Lundberg & Woessner P.A.

(57) ABSTRACT

A system and method include a computer implemented training framework that adapts its behavior to different types of training goals. The system utilizes a measured neuro-physiological state of a student to provide at least one of self regulation feedback and training environment feedback to optimize a learning experience for one or more different types of scenarios.

17 Claims, 4 Drawing Sheets

MULTI PURPOSE CRITERIA BASED ADAPTIVE TRAINING SYSTEM

BACKGROUND

Prior learning systems have attempted to use electric signals, such as electroencephalogram signals to control the difficulty of the material presented to a student. Such systems have had some success in improving the efficiency of learning. These systems are usually designed to work exclusively with a set of goals for training.

SUMMARY

A system and method include a computer implemented training framework that adapts its behavior to different types of training goals. The system utilizes a measured neuro-physiological state of a student to provide both self regulation feedback and training environment feedback to optimize a learning experience for one or more different types of scenarios.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software or a combination of software and human implemented procedures in one embodiment. The software may consist of computer executable instructions stored on computer readable media such as memory or other type of storage devices. Further, such functions correspond to modules, which are software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system.

A system and method utilize a measured neuro-physiological state of a student to provide both self regulation feedback and learning intensity feedback to optimize a learning experience. The system also works with a variety of objective functions. Each objective function of the training may have a different associated desired neuro-physiological state of the student in order to optimize the cost and effectiveness of the training according to the objectives of the training.

In various embodiments, sensors may be used to provide signals representative of the neuro-physiological state of the student to an input. Such signals are converted to digital representations corresponding to whether the student is in a desired learning zone, which is a function of the desired objective function of the training. Self-regulation feedback may be provided to the student to allow the student to modify their own behavior to return to a desired learning zone. In addition, lesson intensity values may be modified based on a current state of the student and historical state. The lesson intensity values may then be used to control the intensity of a learning experience being provided to the student. The system provides adaptive and accelerated training by customizing a training experience to an individual's neurological and physiological response in conjunction with the different objective training functions. Better training may be provided in a faster, lower cost manner. Instructors have a direct indication of off-task students. Instructors may also be remote from students.

Some examples of the different objective functions of the training include: 1. Given a fixed lesson duration, maximizing the amount of processed information; 2. Minimize lesson duration, while maintaining the probability of passing examination on certain passing grade level. 3. Train the student to reach the best possible result of an exercise. 4. Parametric optimization to keep the student within a certain range of parameters, such as keeping brainwaves within a certain range. 5. Best behavior optimization such as a best behavior trajectory recorded earlier by a domain expert or student.

The system and method may be used in many different learning environments, such as in flight simulators and other virtual environments, training systems, class rooms with instructors, military training exercises, systems for treatment of post traumatic stress disorder (PTSD), system for rehabilitation traumatic brain injury patients and many other training environments, and may be optimized based on objective functions specific to desired goals of the training.

Figure 1:
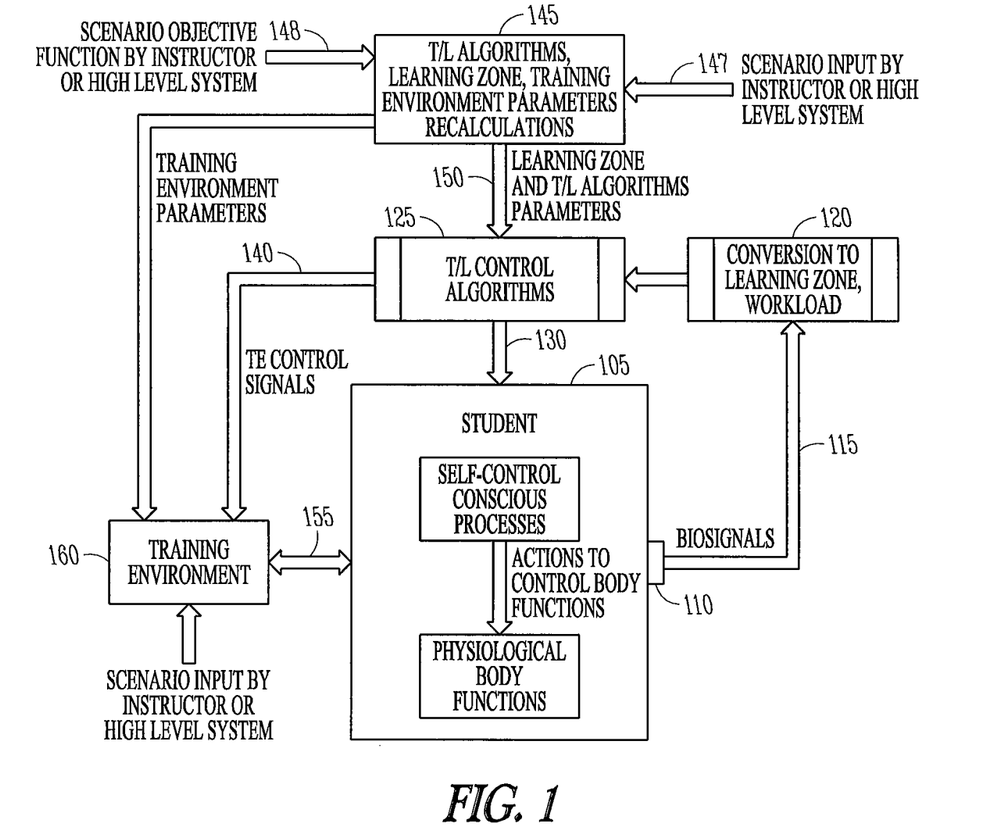
FIG. 1 is a block diagram of a learning system utilizing biofeedback according to an example embodiment.

FIG. 1 is a block diagram of a system 100 that provides a measured neuro-physiological state of a student to provide both self regulation feedback and learning intensity feedback to optimize a learning experience. System 100 also utilizes objective functions of training to modify the desired neuro-physiological state of the student and corresponding optimization of the learning experience. In one embodiment, the system may be referred to as a multi-purpose criteria based adaptive training system (MPCBATS). A student 105 in one embodiment is monitored by a sensor 110. In various embodiments, sensor 110 may measure multiple neuro-physiological signals of the student 105. Sensor 110 in one embodiment includes one or more sensors such as an electroencephalograph (EEG), electrocardiograph (ECG), galvanic skin response (GSR), heart rate variability (HRV), pupilometry, etc. Multiple sensors may be used to decrease noise/signal ratio and improve pattern recognition.

Signals from the sensor 110, are provided at an input 115 to a conversion to learning zone parameters converter 120, which converts the signals to a digital format corresponding to a learning zone. A learning zone may be defined as function of a student's neuro-physiological parameters and range of values for such parameters, where learning is optimal. Deviation from the range may reduce speed and quality of learning.

The neuro-physiological output provided at input 115 from the student 105 is converted to student cognitive parameters, such as level of cognitive workload, level of engagement, alertness, visual engagement, focus, distraction, drowsiness, level of cognitive fatigue, etc. Patterns of the input 115 may be correlated to previous known patterns of an individual student, or even from a group of students to determine the cognitive state of the user to determine whether the student 105 is functioning within a desired learning zone. Such correlation in one embodiment may be done by a controller 125 that is coupled to receive the digital output of converter 120.

Controller 125 in one embodiment performs the above pattern recognition to determine the cognitive/neuro-physiological state of the student 105. In one embodiment, the patterns may comprise up to 10 or more dimensions of neuro-physiological parameters. Other algorithms may be used, such as lookup tables indexed by the digital values, or equations developed based on a history of collected data for individual students or groups of students.

In one embodiment, controller 125 implements control block algorithms that may be recalculated for each different set of objective functions for various training goals. The learning zone may be different for the different objective functions, in both the way in which the learning zone parameters are calculated, and the desired values for the learning zone parameters. In one embodiment, the control algorithms are recalculated in block 145 based on training scenarios input by an instructor or high level system at 147 and objective functions set by an instructor or high level system at 148.

A first feedback loop is indicated at 130. The cognitive/neuro-physiological state may be presented to the student 105 via feedback loop 130, allowing the student to understand what state they are in and use self control in an attempt to alter their state. The controller 125 may provide the state information in the form of a communication, such as visual text, symbols, sound, or other physical stimulus if desired. In addition, the communication may provide suggestions, such as breathing exercises, relaxation techniques, or other suggestions based on standard known self regulation techniques or student specific techniques that have worked. In one embodiment, the communication may just tell the student to "wake up", or "concentrate". Such communications in one embodiment may be provided based on alpha/beta ratios from EEC sensors.

Controller 125 also utilizes the physiological/psychological state signals to determine the cognitive state corresponding to the user's position in relation to the learning zone, and to derive training environment control signals as indicated at 140. Control signals 140 form the start of a second feedback loop. The training environment control signals may have a value indicating that lesson intensity should be decreased or increased depending on the change in learning zone over time and whether the student responded to the feedback 130.

The training environment control signals are provided to a training environment 160, completing a second feedback loop 155. The training environment 160 is representative of any environment where training/learning is desired. Training environment 160 includes virtual environments, such as flight simulators, class rooms with one or more students and a teacher, field exercises, etc. The training environment control signals may be processed to change the speed of the learning experience, change the difficulty of material presented, change the volume or brightness, or control any other controllable parameter of the learning environment to optimize a learning experience.

Generally, if a student is found to be in an optimal learning zone as defined by the control algorithms for a desired training objective, more material may be learned, and the lesson intensity value may be increased until the user begins to transition out of the optimal learning zone. The particular training environment controls may be applied as a function of a goal of optimizing desired parameters to best accomplish the objective functions of the particular training goals. As the user begins to transition out of the optimal learning zone, the first feedback loop 130 may be used to attempt to keep the user in the optimal learning zone prior to modifying the training environment. The use of the first feedback loop 130 and second feedback loop 140, 155 may provide an optimized learning experience tailored to the desired objective function of the particular training desired.

In one embodiment, feedback loop 130 shows student 105 that their parameters deviate from their optimal learning zone, defined as a subset in the individual student's multidimensional physiological/psychological space. The system 100 may suggest actions to try to correct the observable deviation, if any, by having the student use advance self-regulating strategies. Lesson intensity or other training environment factors, such as lighting, sound, and other parameters, may be automatically corrected via a set of intelligent adaptive algorithms based on information from captured real-time training feedback and the student's real-time deviation from the optimal learning zone.

In one example situation where system 100 senses that a student's measure of cognitive workload is not optimal, the system 100 will consider the student's physiological/psychological state in relation to his or her own optimal learning zone, and the history/current state of the student's attempts to stay inside that zone. Based on this information, the system 100 will adjust the lesson by either increasing or decreasing the intensity of the lesson to bring the student into their optimal learning zone.

During training, students may acquire habits of self-regulation, such as the early recognition the symptoms of deviation from optimal learning zone/stress/mental fatigue, together with the application of corresponding mitigation strategies.

In some embodiments, the system may use task and user-independent algorithms to convert physiological data into multiple gauge readings, which show second by second variations in mental activity. These mental state gauges, which currently include cognitive workload, distraction, engagement, and drowsiness, provide insight into an individual's mental processing. The system thus provides objective measures at a rate of once per second that show mental state(s) without interrupting performance.

Each training system satisfies some set of goals. For example, a student's goal may be to retain certain percent of knowledge/skills at the end of a lesson or pass the exam, while the system's goal may be to do the above with minimal cost.

The above may be mathematically expressed as an optimization problem:

Find values of vectors $\vec{T}_{ENV}(t)=\vec{T}_{ENV}^{1}(t)$, $\vec{Z}_{EXS}(t)=\vec{Z}_{EXS}^{1}(t)$, $\vec{L}_{ZONE}(t)=\vec{L}_{ZONE}^{1}(t)$ that minimize value of the objective cost function $$\varphi(\vec{T}_{ENV}^{1}(t), \vec{L}_{ZONE}^{1}(t), \vec{Z}_{EXS}^{1}(t)) = \min_{\vec{T}_{ENV}^{VAR}, \vec{Z}_{EXS}^{VAR}, \vec{L}_{zone}^{VAR}} \varphi(\vec{T}_{ENV}(t), \vec{L}_{zone}(t), \vec{Z}_{EXS}(t)) \quad (1)$$

Subject to the following constraint:

$$Gr(\vec{T}_{ENV}(t), \vec{L}_{zone}(t), \vec{Z}_{EXS}(t)) \geq A, \quad (2)$$

Where:

t—time;

$\vec{T}_{ENV}(t) = (\vec{T}_{ENV}^{VAR}(t), \vec{T}_{ENV}^{PERM}(t))$—vector describing training environment (e.g., virtual, immersive, field exercise, etc.). It consists of two parts—permanent and variable. Variable parts may be independently changed during exercise/lesson (e.g., control system parameters, etc.)

$\vec{Z}_{EXS}(t) = (\vec{Z}_{EXS}^{VAR}(t), \vec{Z}_{EXS}^{PERM}(t))$—vector of lesson/exercise parameters. Permanent part of the vector consists of sensory-motor scenario components and cognitive scenario components multiplied by corresponding weight coefficients. For example, $\vec{Z}_{EXS}^{PERM} = (0.8 \ast \text{sensor-motor}, \_0.1 \ast \text{attention}, \_0.1 \ast \text{alertness}\_)$ describes scenario with prevailing sensory-motor physical activity, while $\vec{Z}_{EXS}^{PERM} = (0.2 \ast \text{sensor-motor}, \_0.8 \ast \text{alertness}\_)$ describes military convoy scenario that requires high levels of alertness as cognitive component. Variable vector part $\vec{Z}_{EXS}^{PERM}$ includes parameters describing independent optimization variables such as lesson speed level, level of complexity, etc;

$\vec{L}_{ZONE}(t) = (\vec{L}_{ZONE}^{VAR}(t), \vec{L}_{ZONE}^{PERM}(t))$—vector describing optimal learning zone. The learning zone is a subset in student's multidimensional physiological/psychological space and expressed by system of inequality equations $$LB(i) \leq PH(i) \leq HB(i), i=1,2 \ldots, n. \quad (3)$$

Each equation defines separate components of the learning zone, where LB(i), HB(i)—values of high and lower border for parameter PH(i). Values LB(i), HB(i) may be calculated based on exercise type (e.g., for scenario with high level of alertness students will be required to produce different levels of $\alpha$, $\theta$ brainwaves compare with scenario with prevailing sensory-motor components).

The objective cost function (1) $\phi(\vec{T}_{ENV}(t), \vec{L}_{zone}(t), \vec{Z}_{EXS}(t))$ defines the cost of training/lesson unit. For simplicity, duration of an exercise/lesson to be minimized may be expressed as:

$$\text{Duration}(\vec{T}_{ENV}(t), \vec{L}_{zone}(t), \vec{Z}_{EXS}(t)) \quad (1A)$$

Constrain function (2) $Gr(\vec{T}_{ENV}(t), \vec{L}_{zone}(t), \vec{Z}_{EXS}(t))$ defines a student's grades dependency from system vectors. Symbol A denotes a passing grade value.

System 100 works with variety of objectives functions. The following is a list of some of the objective functions that may be handled by system 100. Others may also be handled by system 100.

A first objective function presented by equation (1-1A) is designed to minimize lesson duration, while maintaining the probability of passing examination on certain passing grade level (2).

A second objective function is dictated by a fixed lesson duration value and a desire to maximize the amount of processed information. For this objective function, the optimization will may be mathematically represented as:

Find values of vectors $\vec{T}_{ENV}(t) = \vec{T}_{ENV}^1(t)$, $\vec{Z}_{EXS}(t) = \vec{Z}_{EXS}^1(t)$, $\vec{L}_{ZONE}(t) = \vec{L}_{ZONE}^1(t)$ that maximize value of the following objective function $$\psi(\vec{T}_{ENV}^1(t), \vec{L}_{ZONE}^1(t), \vec{Z}_{EXS}^1(t), T) = \quad (4)$$

$$\max_{\vec{T}_{ENV}^{VAR}, \vec{Z}_{EXS}^{VAR}, \vec{L}_{zone}^{VAR}} \psi(\vec{T}_{ENV}(t), \vec{L}_{zone}(t), \vec{Z}_{EXS}(t), T)$$

Subject to the same constraint (2):

$$Gr(\vec{T}_{ENV}(t), \vec{L}_{zone}(t), \vec{Z}_{EXS}(t)) \geq A,$$

Where function $\psi(\ldots)$ calculates amount of processed information, and symbol T denotes fixed value of lesson duration.

To satisfy such criteria, a student needs to operate in a different part of the learning zone, $\vec{L}_{ZONE}(t)$ compared, for example, with a more standard situation described by equations (1)-(1A), (2).

A third objective function results from the desire to train a student to reach the best possible results of an exercise. In this case, the optimization problem may be mathematically represented as:

Find values of vectors $\vec{T}_{ENV}(t) = \vec{T}_{ENV}^1(t)$, $\vec{Z}_{EXS}(t) = \vec{Z}_{EXS}^1(t)$, $\vec{L}_{ZONE}(t) = \vec{L}_{ZONE}^1(t)$ that maximize value of the A in equation (2):

$$Gr(\vec{T}_{ENV}^1(t), \vec{L}_{ZONE}^1(t), \vec{Z}_{EXS}^1(t)) = \quad (5)$$

$$\max_{\vec{T}_{ENV}^{VAR}, \vec{Z}_{EXS}^{VAR}, \vec{L}_{zone}^{VAR}} Gr(\vec{T}_{ENV}(t), \vec{L}_{zone}(t), \vec{Z}_{EXS}(t))$$

A fourth object function involves parametric optimization. A lesson's goal involves the student being required to keep neuro/physiologically values in certain range of values of one to a few $\vec{T}_{ENV}(t)$ or $\vec{L}_{ZONE}(t)$ parameters. For example, as part of self-regulation training, student will be required keep values $\alpha$, $\theta$ brainwaves in a certain range. The mathematical representation is a quadratic optimization problem.

A fifth objective function involves best behavior optimization. A student may be required to follow a best behavior trajectory recorded earlier by a domain expert or by the student or another student in previous exercises. The objective function in case of recorded $\vec{L}_{ZONE}(t)$ trajectory may be expressed mathematically as:

$$\min_{\vec{T}_{ENV}^{VAR}, \vec{Z}_{EXS}^{VAR}, \vec{L}_{zone}^{VAR}} \sum_{i=0}^{N} \left(\vec{L}_{zone}(i\delta T) - \vec{L}_{ZONE}^{BEST}(i\delta T)\right)^2, i = 0, 1, \ldots, N \quad (7)$$

Further objective functions may involve team exercises or any other function designed to achieve a desired training result. There are many different possibilities for tailoring the system 100 to accomplish desired training objectives utilizing many different training environments.

Figure 2:
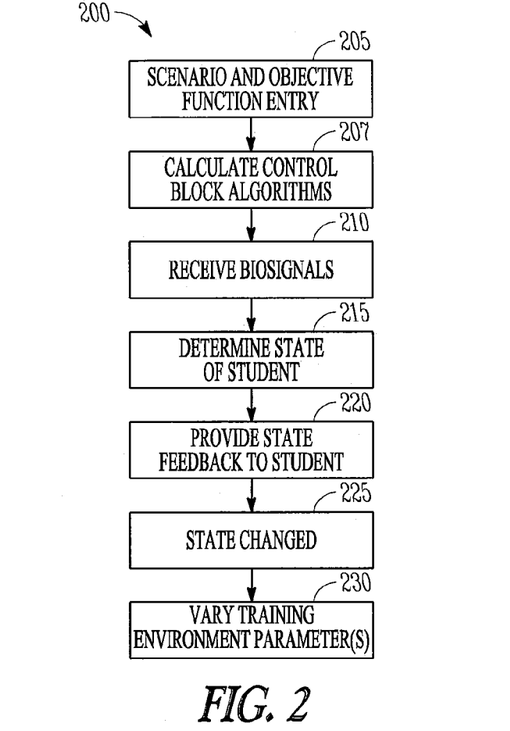
FIG. 2 is a flowchart indicating a method of providing multiple levels of feedback in a training environment according to an example embodiment.

An events sequence during initial scenario entry or on system startup is illustrated in flowchart 200 form in FIG. 2. In one embodiment, the method 200 is implemented by a computer system. After an instructor or high level system enters a new scenario and chosen objective function at 205, the system recalculates control block algorithms, $\vec{L}_{ZONE}(t)$ parameters, etc., at 207.

At 210, biosignals representative of a neuro-physiological state of a student are received. A current neuro-physiological state is determined at 215 using the received biosignals. In various embodiments, the biosignals include many different measurements of the physiological and psychological state of the student. At 220, feedback is provided to the student as a function of the neuro-physiological state of the student as determined from the biosignals. The feedback is also a function of the objective functions defined for the particular exercise. If the neuro-physiological state of the student has changed as indicated at 225 following provision of the feedback, further feedback may be provided by modifying training environment factors, such as a lesson intensity value as a function of the neuro-physiological state of the student at 230 and providing the modified lesson intensity value to the training environment 160. Both feedback loops are controlled by the particular control algorithms developed to meet the objective functions of one of several different sets of objective functions.

Several variations may be seen in further embodiments. If the student maintains an optimal learning cognitive state, no feedback may be provided. Alternatively, the student may be provided feedback about his or her cognitive state so that they understand they are in a good state. The intensity level may also be manipulated in some embodiments such that it gradually increases to further optimize the learning experience. The gradual increase may continue until a detrimental change in the cognitive state is detected, at which point cognitive state feedback may be provided to the user followed by a reduction in intensity if the detrimental change in cognitive state does not improve. Alternatively, if the cognitive state feedback worked to return the student to an optimal learning cognitive state, a training environment parameter such as intensity may again be increased, or held constant if desired.

In further embodiments, natural biorhythms of students may be taken into account in both determining the cognitive state of the student and in providing cognitive state feedback and learning intensity feedback. Providing both types of feedback enables the use of many different control algorithms which may utilize one or more biosignals. Great flexibility in the algorithms may be provided in various embodiments. The algorithms may be generated in one embodiment by performing regression analysis of multiple parameters that are relevant in the optimizations for each overall objective function. This results in different control algorithms for each objective function to be accomplished.

Figure 3:
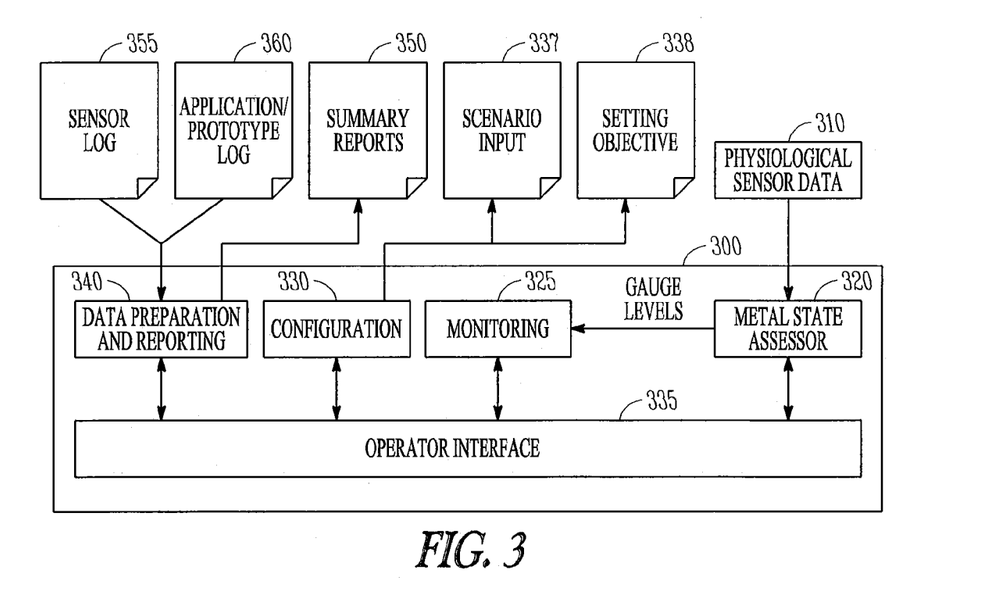
FIG. 3 is a block architectural diagram of a mental state assessor according to an example embodiment.

FIG. 3 is a block diagram of a sensor based mental assessment system 300 according to an example embodiment. Physiological sensor data is generated or received at 310 and provided to the system 300. In various embodiments, the sensor data may include one or more of EEG, EKG, GSR and pupilometry. Other sensors may be used in further embodiments, such as body temperatures, oxygen levels, blood sugar levels, and many others if desired.

System 300 includes a mental state assessor 320 that receives the sensor data and assesses the mental state represented by the sensor data. The mental state may be determined by many different algorithms, including the use of empirical observations of students and correlating such observations to the sensor data. The mental state may be tailored to each individual student in one embodiment. Mental state gauges may be provided at a monitoring module 325, which may provide graphical indications of different mental states, such as cognitive workload, visual engagement, distraction, drowsiness and others. At a configuration module 330, the system 300 may be configured to allow operators, via an operator interface 335 to manually enter non-logged events in real time, and to set objectives at 337 and input scenarios at 338. The ability to set objectives and input scenarios allows different objective functions of training to be identified and system control algorithms to be modified according to the scenarios and objective functions.

Many different data preparation and reporting functions may be available as indicated at 340 to provide summary reports 350, sensor logs 355 and application/prototype logs 360. In one embodiment, a real-time estimate of cognitive workload may be provided.

In one embodiment, learning optimization may be provided based on a student's state of cognitive workload value W(t), t—time, in accordance with the objective functions and corresponding optimizations.

Intensity of lessons may be a function of the number of tasks given to a student per a certain time period. A new set of tasks appears on the screen after the time period expires. In one example, there may be 10 levels of intensity. Level one consists of a single task; level two consists of two tasks, and so on.

For calculating student's state of cognitive workload, a set of EEG sensors may be placed on student's scalp. A raw EEG signal, polled with frequency 256 Hz, after filtration and removal artificial effects (e.g., eyes blinking), is converted to values of amplitudes for different frequencies by using a FFT (Fast Fourier Transformation) algorithm.

In one embodiment, the following standard frequencies: $\alpha$ is in the range 8-12 Hz, $\beta$ is the range of 12-30 Hz, $\gamma$ is the range of 30-100 Hz, $\theta$ is the range of 4-7 Hz and $\delta$ is the range 0-4 Hz may be used. Conversion to a value of workload W(t) may be done according to the following formula:

$$W(t-n) = k_1\alpha(t-n) + k_2\beta(t-n) + k_3\gamma(t-n) + k_4\theta(t-n) + k_4\delta(t-n) + k_5\alpha(t-n)/\theta(t-n) + k_6\gamma(t-n)/\alpha(t), n = 0, 1, 2, \ldots, m \quad (1)$$

$$W(t) = \sum_{i=0}^{m} r_i W(t-i)$$

Where—$k_i$—conversion coefficients for different frequencies $\alpha(t), \beta(t), \gamma(t), \theta(t), \delta(t)$; $r_i$—weight coefficients.

For regulation lesson's intensity level a proportional integral controller may be used:

$$Y(n) = k_1(W(n) - W_{set}) + \sum_{i=0}^{n} k_2(W(i) - W_{set}) \quad (2)$$

Where Y(n) corresponds to a lesson's intensity on step n, W(n) corresponds to a measured value of workload on step n; $W_{set}$ corresponds to an initial workload value, $k_1, k_2$ are coefficients for proportional and integral parts of the controller. Discrete integer values of intensity are obtained by rounding output Y(t) to the integer value: $Y_{current}$=ROUND(Y(n)), where ROUND( ) is the standard rounding function.

Block 145 recalculates values of learning zone parameters, training environment parameters and algorithm's parameters based on input 148 of objective function and input 147 of a scenario. In one example, consider objective function is used, that minimizes lesson duration, while maintaining the probability of passing examination with certain passing grade level defined by functions (1A), (2). In one embodiment general objective function (1A) is represented by the following empirical equation:

$$\min_{\mu,\sigma}\left(k_1\exp\left\{(k_2(\vec{Z}_{EXS}^{perm})\mu - k_3(\vec{Z}_{EXS}^{perm})\sigma)\frac{1}{\chi}\right\}\right) \quad (3A)$$

Grade passing zone formula (2) is replaced by the following system of equations:

$$\sigma > k_4\ln\left(k_5\mu\frac{1}{\chi}\right) \quad (3B)$$

$$\sigma < k_4\ln\left(k_5\mu\frac{1}{\chi}\right) + k_6$$

Where: $k_i$—coefficients, $\mu$—scenario's starting set level of intensity (e.g. complexity, speed, etc.), $\sigma$-$\alpha$, $\theta$ brainwaves ratio (it best correlates with student's attention level—one of important parameter of learning zone). Coefficients $k_2$ ($\vec{Z}_{EXS}^{perm}$), $k_3$ ($\vec{Z}_{EXS}^{perm}$) are functions of vector $\vec{Z}_{EXS}^{PERM}$—permanent part of vector of lesson/exercise parameters.

The above optimization problem (3A-B) has a numerical solution with good initial approximation defined by finding local maximum of (3A), $\chi$—student's capability index defined in relation to standard Bell curve and based on the student's corresponding historical data.

The whole system functions in the following way: First, after input of an objective function and a scenario, block 145 calculates optimal values of learning zone parameters, training environment parameters and, in some cases, algorithms parameters. In case of embodiment, defined by equations (3A), (3B) block 145 calculates values of learning zone parameter alpha/theta denoted by symbol $\sigma$ and initial value of lesson's intensity $\mu$. After setting these values the system automatically turned on.

If the system detects a change in workload value W(t), then in the case where workload W(t) is going down during specified time period P and passes through a threshold value T RH: W(t)−W(t+P)>=TRS, then the system turns on the controller. As a result, a lesson's intensity will be increased and, with delay workload value W(t) will also increase.

In case if W(t) is going up: W(t+P)−W(t)>=TRS, then the system will send a message to the student about increasing workload value in the form of a text message/graphic icon with numerical or symbolic value on computer screen overlay and/or sound.

In addition, to the message, the system may provide suggestions, such as breathing exercises, relaxation techniques, or others. The messages may depend on detected neurophysiological states, sensed by other sensors and a value of W(t) decrement. Then, after giving the student time period K(t) for normalization of W(t) value. K(t) value depends on value of W(t) decrement and student's personal history. Then if after time period K(t) value W(t) not normalized, the system turned on controller (2), which decrease lesson's intensity level.

In a further embodiment, learning optimization may be provided based on states of a student's cognitive alertness A(t) and level of engagement E(t), t—time. The only differences between the embodiment and the previous embodiment are discussed below.

For calculating cognitive alertness and level of cognitive engagement, multiple sensors such as EEG, EKG, and GSR may be used. Conversion to the value of cognitive alertness A(t) may be done in according to the following regression type formula:

$$A(t-n) = k_1\alpha(t-n)/\theta(t-n) + k_2\gamma(t-n)/\alpha(t) + k_3 ekg(t-n) + \quad (3)$$
$$k_4 ekg(t-n)^{1/2} + k_5 gsr(t-n) + k_6 gsr(t-n)^3, n = 0, 1, 2, \ldots, m$$

$$A(t) = \sum_{i=0}^{m} r_i A(t-i)$$

Where—$k_i$—conversion coefficients for different frequencies $\alpha(t), \beta(t), \gamma(t), \theta(t), \delta(t)$; ekg(t) refer to EKG sensors measurements; gsr(t)—GSR measurements; $r_i$—weight coefficients. We are using similar regression formula for conversion EEG, EKG, and GSR sensors measurements to level of engagement E(t) value.

Based on a student's cognitive alertness A(t) and level of engagement E(t) values a student's position in relation to optimal learning zone LZ(t) may be calculated by employing the following regression formula:

$$LZ(t-n) = \sum_{m=0}^{3} k_m^a A(t-n)^m + \sum_{m=0}^{3} k_m^e E(t-n)^m, \quad (4)$$

$$n = 0, 1, 2, \ldots, s$$

$$LZ(t) = \sum_{i=0}^{m} r_i LZ(t-i)$$

Where—k—regression coefficients, $r_i$—weight coefficients.

An LZ(t) normal range is between $LZ_{min}<=LZ(t)<=LZ_{max}$. In one embodiment for regulation of a lesson's intensity level, a proportional integral controller may be used:

$$Y(n) = k_1(LZ(n) - LZ_{set}) + \sum_{i=0}^{n} k_2(LZ(i) - LZ_{set}). \quad (5)$$

The whole system functioning is in according to the description for the previous embodiment, where workload value W(t) is replaced by learning zone value LZ(t).

Figure 5:
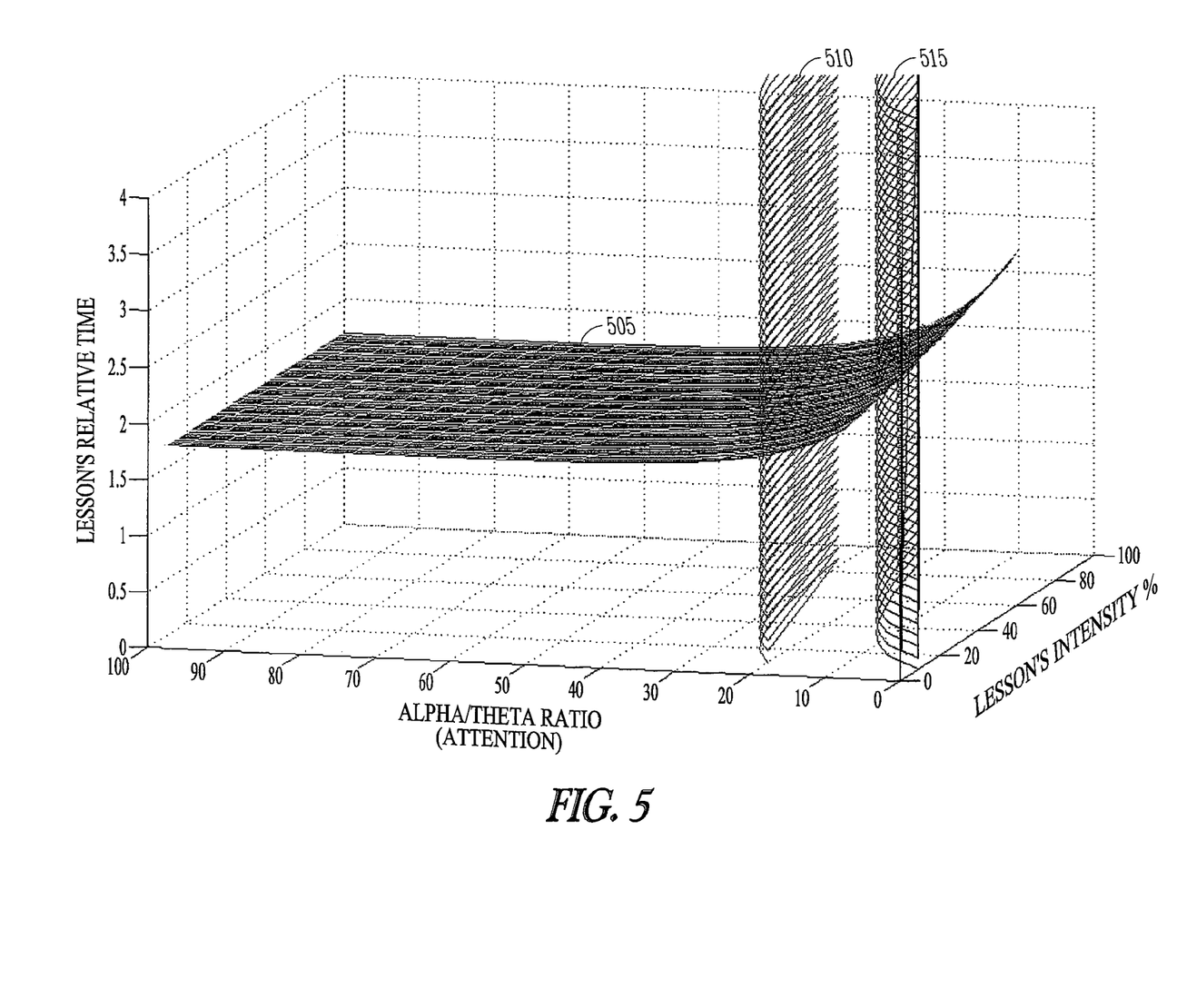
FIG. 5 presents a graphical illustration of finding a solution as a function of scenario and specific training objective according to an example embodiment.

FIG. 5 presents a graphical illustration of finding a solution to the optimization problem in one example embodiment. The vertical axis presents values (lesson's relative time) of objective function (3A) at 505 as function of the lesson's intensity and alpha/theta brainwaves ratio (attention). The two vertical shapes 510 and 515 correspond to equations (3B). All possible solutions of optimization problems belong to the region of objective function they limit.

Figure 4:
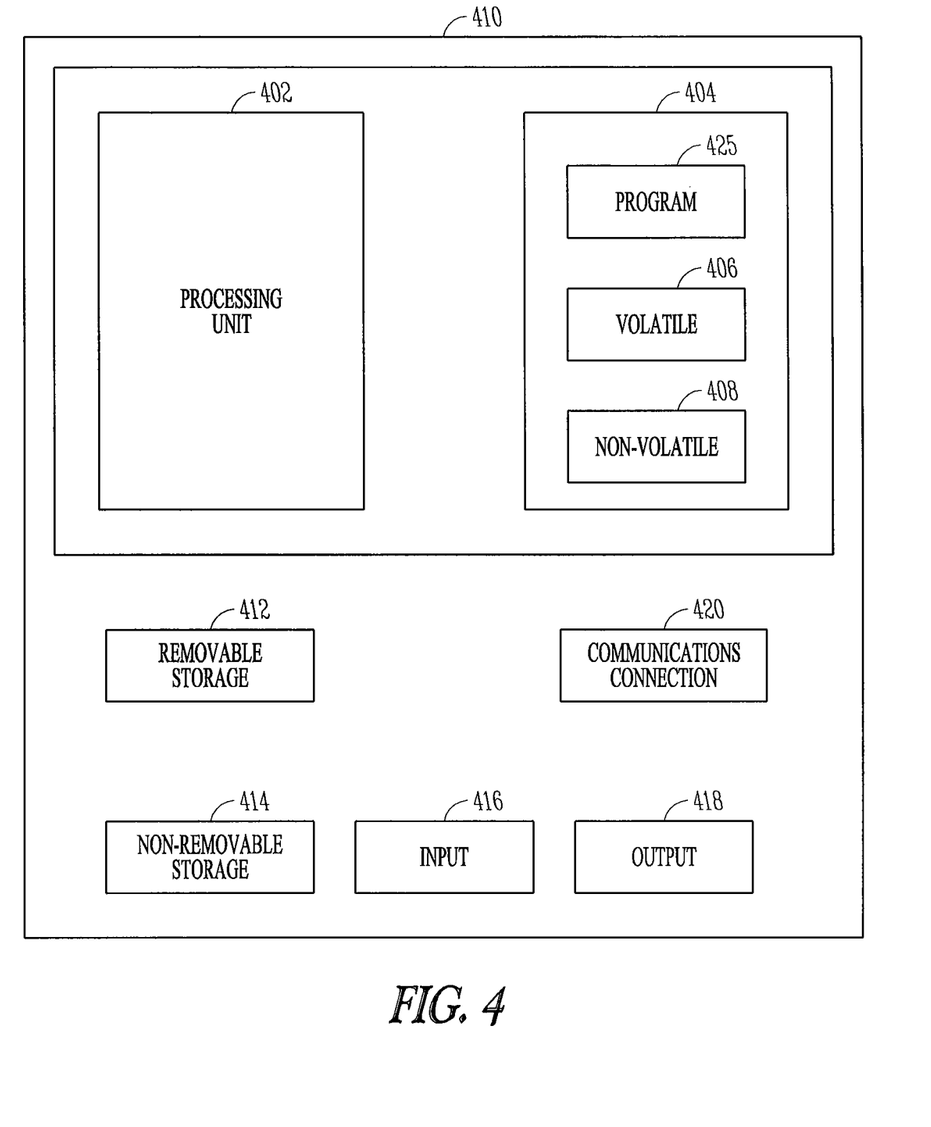
FIG. 4 is a block diagram of a specifically programmed computer system for executing methods and algorithms according to an example embodiment.

A block diagram of a computer system that executes programming for performing the above methods and algorithms is shown in FIG. 4. A general computing device in the form of a computer 410, may include a processing unit 402, memory 404, removable storage 412, and non-removable storage 414. Memory 404 may include volatile memory 406 and non-volatile memory 408. Computer 410 may include—or have access to a computing environment that includes—a variety of computer-readable media, such as volatile memory 406 and non-volatile memory 408, removable storage 412 and non-removable storage 414. Computer storage includes random access memory (RAM), read only memory (ROM), erasable programmable read-only memory (EPROM) & electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions. Computer 410 may include or have access to a computing environment that includes input 416, output 418, and a communication connection 420. The computer may operate in a networked environment using a communication connection to connect to one or more remote computers. The remote computer may include a personal computer (PC), server, router, network PC, a peer device or other common network node, or the like. The communication connection may include a Local Area Network (LAN), a Wide Area Network (WAN) or other networks.

Computer-readable instructions stored on a computer-readable medium are executable by the processing unit 402 of the computer 410. A hard drive, CD-ROM, and RAM are some examples of articles including a computer-readable medium.

The Abstract is provided to comply with 37 C.F.R. §1.72(b) is submitted with the understanding that it will not be used to interpret or limit the scope or meaning of the claims.

The invention claimed is:

1. A sensor system comprising:
a sensor input to couple to an electroencephalograph sensor to detect a neuro-physiological state of a student;
a configurator input to receive information regarding training objective functions and to modify control algorithms and system parameters in accordance with a selected training objective function; and
a controller coupled to the sensor input to implement the control algorithms and provide a communication if the student is outside a desired neuro-physiological state consistent with a desired learning zone and to provide a lesson intensity control signal as a function of the provided communication, sensed neuro-physiological state and selected training objective function;
a converter to convert the sensed neuro-physiological state of the student to cognitive parameters that are representative of cognitive workload, level of engagement, and alertness and wherein the lesson intensity is regulated using proportional integral control as a function of workload calculated from the sensed neuro-physiological state;
wherein the controller calculates the cognitive workload as a function of the amplitudes of the electroencephalograph signal at multiple electroencephalograph signal frequencies; and
wherein the electroencephalograph signal frequencies include: $\alpha$ corresponding to a range 8-12 Hz, $\beta$ corresponding to a range of 12-30 Hz, $\gamma$ corresponding to a range of 30-100 Hz, $\theta$ corresponding to a range of 4-7 Hz and $\delta$ corresponding to a range 0-4 Hz, and wherein the controller is configured to calculate workload, W(t), at time, t, according to the following formula:

$$W(t-n) = k_1\alpha(t-n) + k_2\beta(t-n) + k_3\gamma(t-n) + k_4\theta(t-n) + k_4\delta(t-n) + \frac{k_5\alpha(t-n)}{\theta(t-n)} + \frac{k_6\gamma(t-n)}{\alpha(t)}, n = 0, 1, 2, \ldots m$$

$$W(t) = \sum_{i=0}^{m} r_i W(t-i)$$

where $k_i$ are conversion coefficients for different frequencies $\alpha(t), \beta(t), \gamma(t), \theta(t), \delta(t)$ and $r_i$ are coefficients.

2. The system of claim 1 wherein the sensor input is configured to receive input from multiple sensors selected from the group consisting of an electroencephalograph, electrocardiograph, galvanic skin response sensor, heart rate variability sensor and pupilometry sensor.

3. The system of claim 1 wherein the cognitive parameters are representative of cognitive workload.

4. The system of claim 3 wherein the controller correlates the cognitive parameters to known patterns of such cognitive parameters to determine whether the student is within the desired learning zone consistent with the selected training objective function.

5. The system of claim 4 wherein the known patterns are patterns specific to historical performance of the student.

6. The system of claim 1 wherein the communication comprises information on self regulation techniques to improve the neuro-physiological state.

7. The system of claim 1 wherein the lesson intensity control signal causes modification of at least one of volume or brightness of a learning environment.

8. The system of claim 1 wherein the selected training objective functions are switchable between at least two training objective functions selected from a fixed lesson duration while maximizing information processed, training to reach the best possible results of an exercise, optimizing parameters corresponding to the learning environment or learning zone, minimizing lesson duration while maintaining a probability of obtaining desired examination results, and following a best behavior trajectory training objective function.

9. A system comprising:
a sensor input to receive biosignals representative of a neuro-physiological state of a student;
a converter coupled to the sensor input to receive the biosignals and to convert the biosignals to learning zone digital values;
a training environment for the student responsive to lesson intensity values;
a configurator to receive input regarding training objective functions and to modify control algorithms in accordance with the training objective functions; and
a controller coupled to the converter to receive the learning zone digital values and to provide a communication to the student if the learning zone digital values are indicative of the student being outside a desired neuro-physiological state consistent with the control algorithms and to modify the training environment as a function of the control algorithms and sensed neuro-physiological state;
a converter to convert the sensed neuro-physiological state of the student to cognitive parameters that are representative of cognitive workload, level of engagement, and alertness and wherein the lesson intensity is regulated using proportional integral control as a function of workload calculated from the sensed neuro-physiological state;
wherein the controller calculates the cognitive workload as a function of amplitudes of the electroencephalograph signal at multiple electroencephalograph signal frequencies; and
wherein the electroencephalograph signal frequencies include: $\alpha$ corresponding to a range 8-12 Hz, $\beta$ corresponding to a range of 12-30 Hz, $\gamma$ corresponding to a range of 30-100 Hz, $\theta$ corresponding to a range of 4-7 Hz and $\delta$ corresponding to a range 0-4 Hz, and wherein the controller is configured to calculate workload, W(t), at a time, t, according to the following formula:

$$W(t-n) = k_1\alpha(t-n) + k_2\beta(t-n) + k_3\gamma(t-n) + k_4\theta(t-n) +$$
$$k_4\delta(t-n) + \frac{k_5\alpha(t-n)}{\theta(t-n)} + \frac{k_6\gamma(t-n)}{\alpha(t)}, n = 0, 1, 2, \ldots m$$
$$W(t) = \sum_{i=0}^{m} r_i W(t-i)$$

where $k_i$ are conversion coefficients for different frequencies $\alpha(t)$, $\beta(t)$, $\gamma(t)$, $\theta(t)$, $\delta(t)$ and $r_i$ are coefficients.

10. The system of claim 9 wherein the controller provides lesson intensity values as a function of current and historical lesson intensity values.

11. The system of claim 9 wherein the training environment is a computer controlled training environment.

12. The system of claim 9 wherein the training environment is a computer simulation.

13. The system of claim 9 wherein the training environment is a classroom.

14. The system of claim 9 wherein the received biosignals correspond to biosignals generated by multiple sensors selected from the group consisting of an electroencephalograph, electrocardiograph, galvanic skin response sensor, heart rate variability sensor and pupilometry sensor.

15. The system of claim 9 wherein the communication comprises information on self regulation techniques to improve the neuro-physiological state of the student.

16. A computer implemented method comprising:
configuring a controller executing on a computer system with control algorithms, stored on a computer readable storage device, as a function of a selected objective function and training scenario;
receiving biosignals to produce received biosignals representative of a neuro-physiological state of a student;
determining via the computer system, a current neuro-physiological state from the received biosignals;
modifying, via the computer system, a training environment as a function of the current neuro-physiological state of the student based on the control algorithms; and
converting the sensed neuro-physiological state of the student to cognitive parameters that are representative of cognitive workload, level of engagement, and alertness and wherein the lesson intensity is regulated using proportional integral control as a function of the cognitive workload calculated from the sensed neuro-physiological state;
wherein the cognitive workload is calculated as a function of amplitudes of the electroencephalograph signal at multiple electroencephalograph signal frequencies; and
wherein the electroencephalograph signal frequencies include: $\alpha$ corresponding to a range 8-12 Hz, $\beta$ corresponding to a range of 12-30 Hz, $\gamma$ corresponding to a range of 30-100 Hz, $\theta$ corresponding to a range of 4-7 Hz and $\delta$ corresponding to a range 0-4 Hz, and wherein the controller is configured to calculate workload, W(t), at a time, t, according to the following formula:

$$W(t-n) = k_1\alpha(t-n) + k_2\beta(t-n) + k_3\gamma(t-n) + k_4\theta(t-n) +$$
$$k_4\delta(t-n) + \frac{k_5\alpha(t-n)}{\theta(t-n)} + \frac{k_6\gamma(t-n)}{\alpha(t)}, n = 0, 1, 2, \ldots m$$
$$W(t) = \sum_{i=0}^{m} r_i W(t-i)$$

where $k_i$ are conversion coefficients for different frequencies $\alpha(t)$, $\beta(t)$, $\gamma(t)$, $\theta(t)$, $\delta(t)$ and $r_i$ are coefficients.

17. The system of claim 1 wherein the lesson intensity value is calculated by the controller in accordance with: $Y(n) = k_1(W(n) - W_{set}) + \Sigma_{i=0}^{n} k_2(W(i) - W_{set})$ where Y(n) corresponds to a lesson's intensity on step n, W(n) corresponds to a measured value of workload on step n, $W_{set}$ corresponds to an initial workload value, and $k_1$, $k_2$ are coefficients for proportional and integral parts of the controller.

* * * * *